United States Patent [19]
Daneshvar

[11] Patent Number: 5,205,282
[45] Date of Patent: Apr. 27, 1993

[54] THERAPEUTIC NASAL INHALATOR

[76] Inventor: Yousef Daneshvar, 33200 Slocum, Farmington, Mich. 48024

[21] Appl. No.: 792,688

[22] Filed: Nov. 15, 1991

[51] Int. Cl.⁵ .................. A61M 16/00; H05B 3/12
[52] U.S. Cl. ................. 128/203.26; 128/203.12; 128/204.14; 4/537
[58] Field of Search .......... 128/204.14, 203.16, 128/207.18, 203.12, 203.26, 730, 200.24, 203.15, 203.18, 203.29, 204.12, 204.17; 4/537

[56] References Cited

U.S. PATENT DOCUMENTS

| | | | |
|---|---|---|---|
| 43,536 | 7/1864 | Vergnes | 128/203.15 |
| 261,400 | 7/1882 | Souvielle | 128/204.14 |
| 279,091 | 6/1883 | Goldberg | 128/203.16 X |
| 670,084 | 3/1901 | Sloane | 128/203.26 |
| 1,021,865 | 4/1912 | Fries | 128/203.29 X |
| 1,085,833 | 2/1914 | Wilson | 128/204.14 X |
| 1,112,312 | 9/1914 | Oliva | 128/203.29 X |
| 1,186,308 | 5/1916 | Gudger | 128/203.29 X |
| 1,221,516 | 4/1917 | Devilbiss | 128/203.16 X |
| 2,214,032 | 9/1940 | Stewart | 128/203.15 |
| 2,579,362 | 10/1946 | Cage | 128/204.14 X |
| 4,621,641 | 11/1986 | Frank | 4/537 X |
| 4,903,850 | 2/1990 | Frank | 4/537 X |
| 5,148,801 | 9/1992 | Douwens | 128/203.16 |

FOREIGN PATENT DOCUMENTS

| | | | |
|---|---|---|---|
| 3707659 | 9/1988 | Fed. Rep. of Germany | 128/203.26 |
| 340398 | 2/1904 | France | 128/203.26 |
| 6323 | of 1888 | United Kingdom | 128/203.16 |
| 742543 | 12/1955 | United Kingdom | 128/203.26 |
| 8602276 | 4/1986 | World Int. Prop. O. | 128/203.16 |

Primary Examiner—Edgar S. Burr
Assistant Examiner—Eric P. Raciti

[57] ABSTRACT

An enclosure formed by a pan and a cover is divided into an upper steam chamber and a lower hot water chamber by a perforate partition. Steam rises through the perforate partition from the hot water chamber to the steam chamber. The cover has a nose aperture into which a user places the nose to inhale steam from the steam chamber. The steam chamber is selectively communicated to the surrounding space on its exterior to control the direction and the amount of airflow between the steam chamber and the exterior. The amount is controlled by a multi-apertured disk on the exterior and the direction by a slide on the interior which can select either bi-directional flow or uni-directional flow in the direction into the chamber.

20 Claims, 6 Drawing Sheets

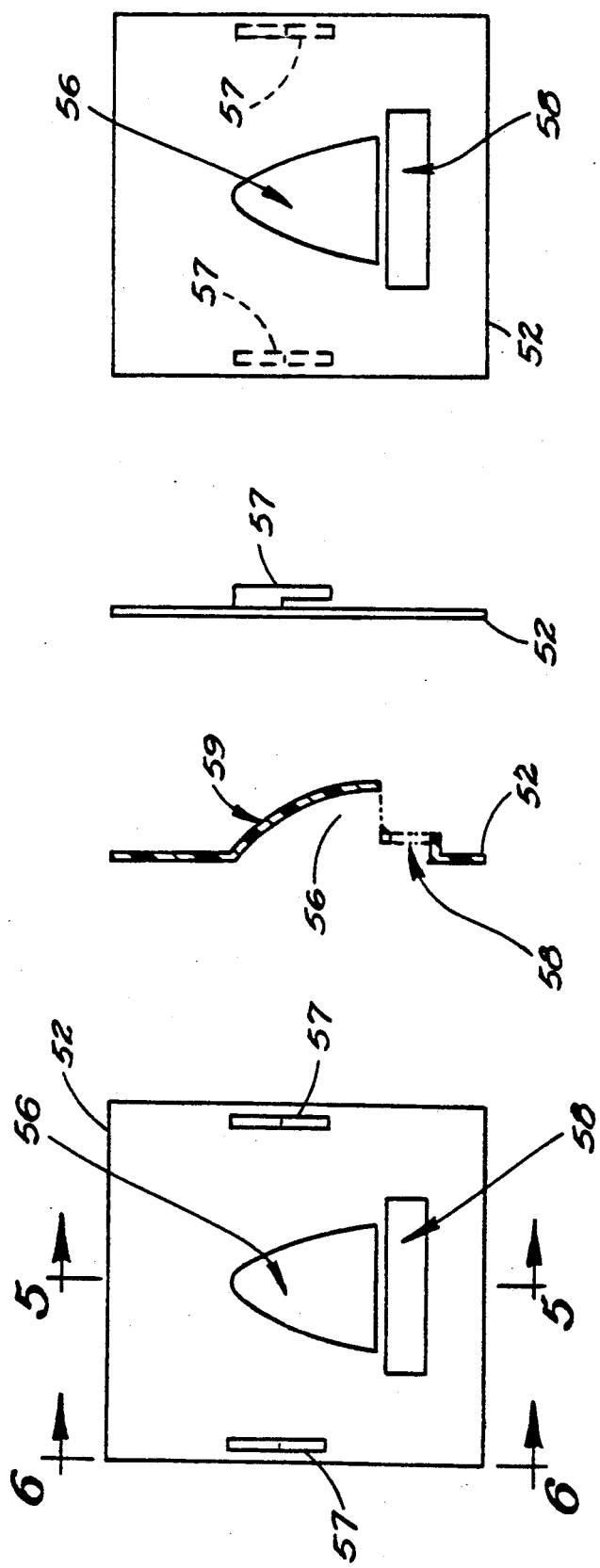

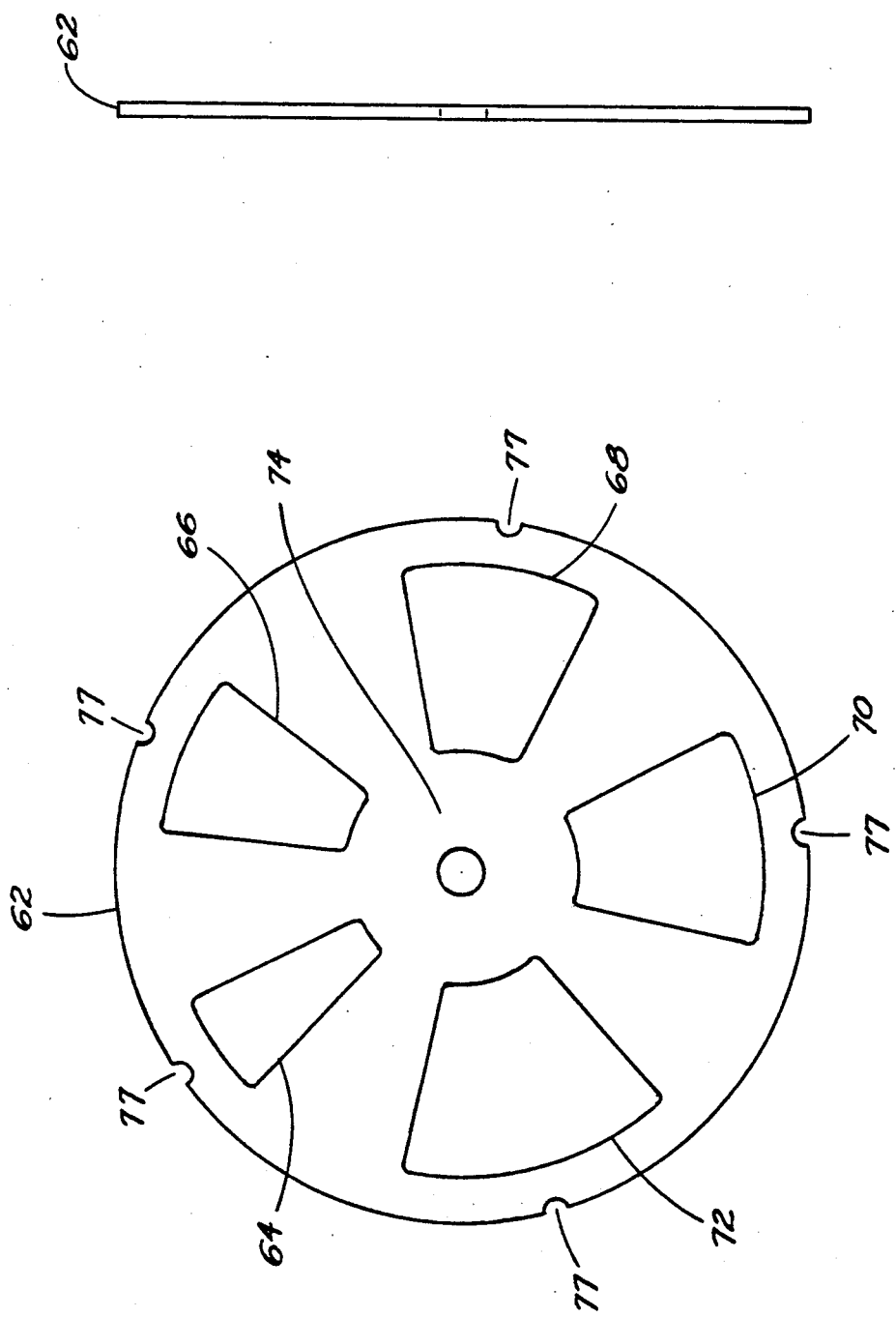

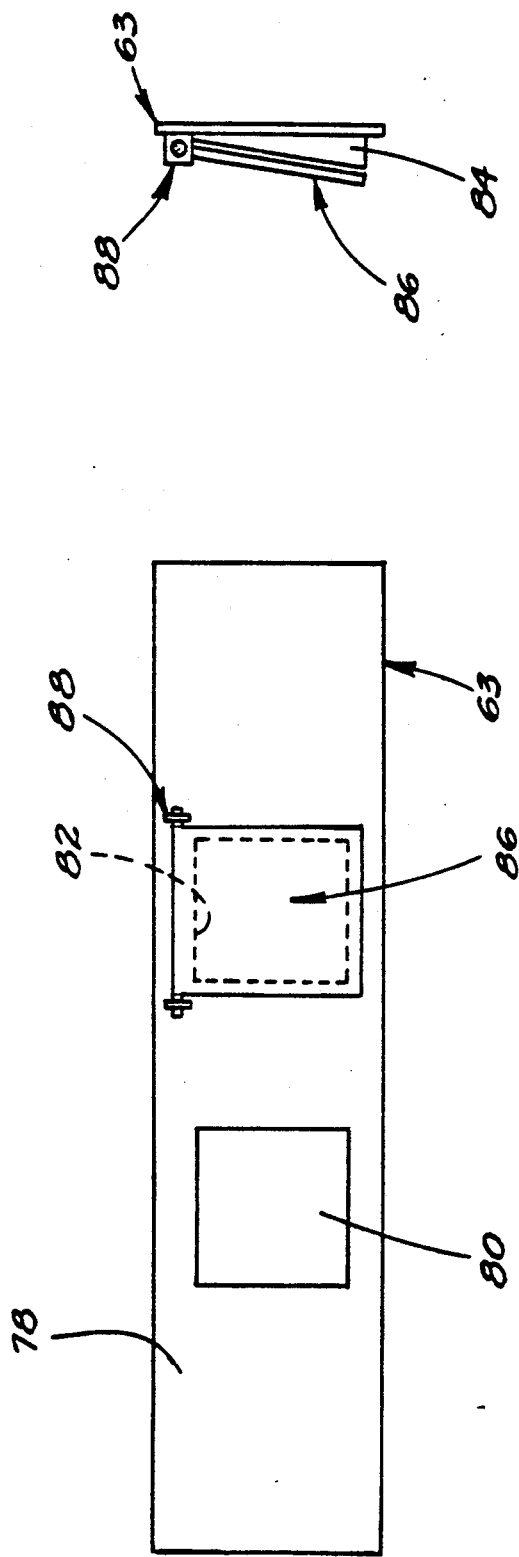

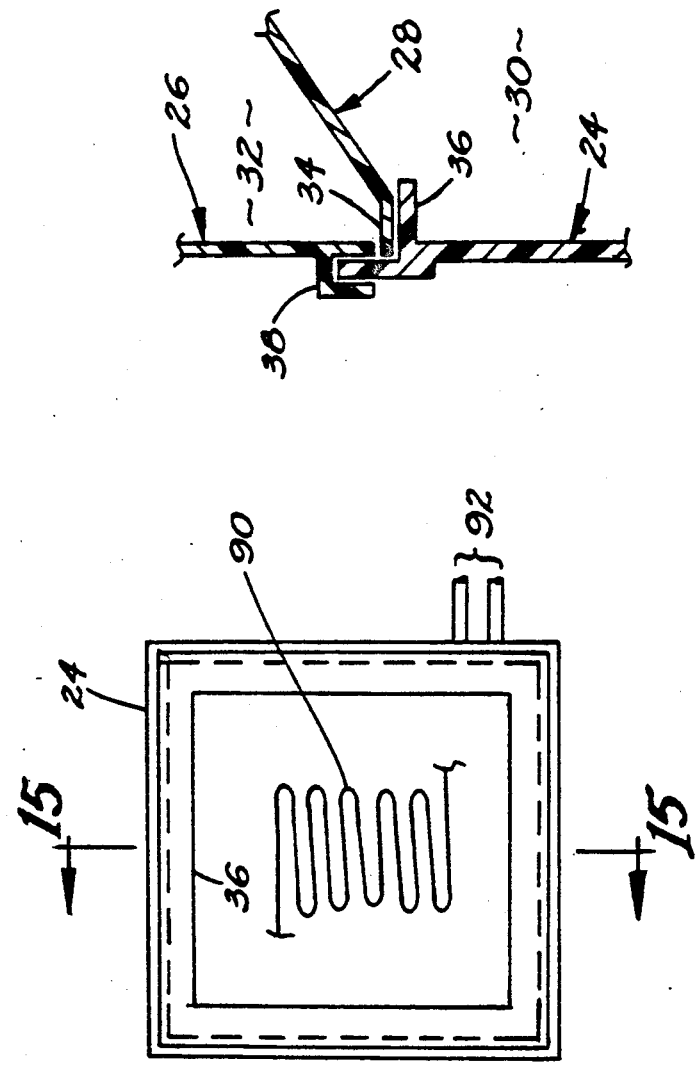

THERAPEUTIC NASAL INHALATOR

FIELD OF THE INVENTION

This invention relates generally to therapeutic apparatus, and particularly to a device that is useful for relieving nasal and sinus congestion.

BACKGROUND OF THE INVENTION

Many people suffer nasal and sinus congestion, and it is known that the inhalation of warm moist air, steam in particular, can be an effective therapy for providing relief. Various forms of therapeutic apparatus for generating steam to provide such treatment are known. Examples are found in the following patent documents: U.S. Pat. Nos. 261,400; 279,091; 1,085,833; 1,221,516; and 2,579,362; WIPO 8602276; and U.K. 6323.

The present invention relates to a new and useful form of this general type of therapeutic apparatus.

SUMMARY OF THE INVENTION

Briefly, a preferred embodiment of the invention comprises an enclosure which is cooperatively defined by an open-top pan and an open-bottom cover that are separably secured together. The pan forms a liquid containing chamber for holding hot water that generates steam. The cover forms a steam collecting chamber for steam that is generated by the hot water in the pan. A perforate partition is disposed between the pan and the cover to allow the steam vapors to convectively rise from the lower liquid containing chamber into the upper steam collecting chamber while at the same time providing some degree of protection against hot liquid water in the lower chamber splashing or otherwise intruding into the upper chamber. The pan is shaped to allow its placement on a flat horizontal surface, such as a table top. The cover comprises a first wall portion that contains a nose aperture for allowing a user to insert his nose into the upper chamber and inhale steam therefrom. The cover also comprises a second wall portion that contains means for selectively communicating the upper chamber to the surrounding exterior space outside the enclosure. This means for selectively communicating the upper chamber to the surrounding exterior space comprises a multi-apertured rotary member on the exterior and a selectively positionable slide assembly on the interior. The multi-apertured rotary member is selectively positionable to select a particular one of its differently sized apertures through which the upper chamber can communicate to the surrounding exterior space. The selectively positionable slide assembly is selectively positionable to select through the selected aperture of the rotary member, either bi-directional communication of the upper chamber with the surrounding exterior space, or uni-directional communication. The selection of uni-directional communication allows flow only in the direction into the upper chamber from the surrounding exterior space, and this feature is provided by a one-way valve mechanism on the slide assembly.

Further details of the invention will be seen in the following detailed description which is accompanied by drawings.

BRIEF DESCRIPTION OF THE DRAWINGS

FIG. 4 is a rear elevational view of one part of the apparatus of FIG. 1.

FIG. 5 is a vertical sectional view along line 5—5 in FIG. 4.

FIG. 6 is a side elevational view in the direction of arrows 6—6 in FIG. 4.

FIG. 7 is a front elevational view of the part of FIG. 4.

FIG. 8 is an enlarged elevational view of another of the parts.

FIG. 9 is a side elevational view of the part of FIG. 8.

FIG. 10 is an enlarged elevational view of yet another of the parts.

FIG. 11 is a right side elevational view of FIG. 10.

FIG. 15 is a fragmentary cross sectional view in the direction of arrows 15—15 in FIG. 16.

FIG. 16 is a top plan view in the direction of arrows 16—16 in FIG. 3.

FIG. 17 is an enlarged fragmentary cross sectional view in the direction of arrows 17—17 in FIG. 3.

DESCRIPTION OF THE PREFERRED EMBODIMENT

Figure 3:
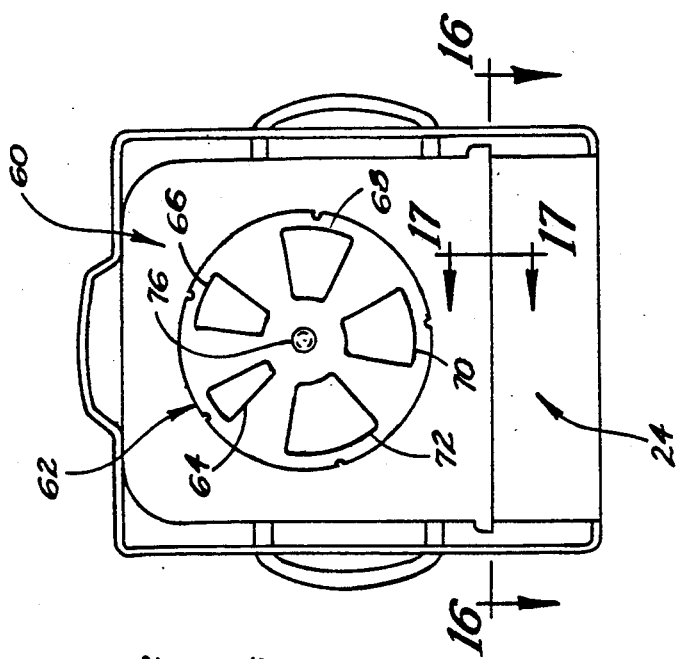
FIG. 3 is a rear elevational view of FIG. 1 with a few elements omitted for patent drawing purposes.
Figure 2:
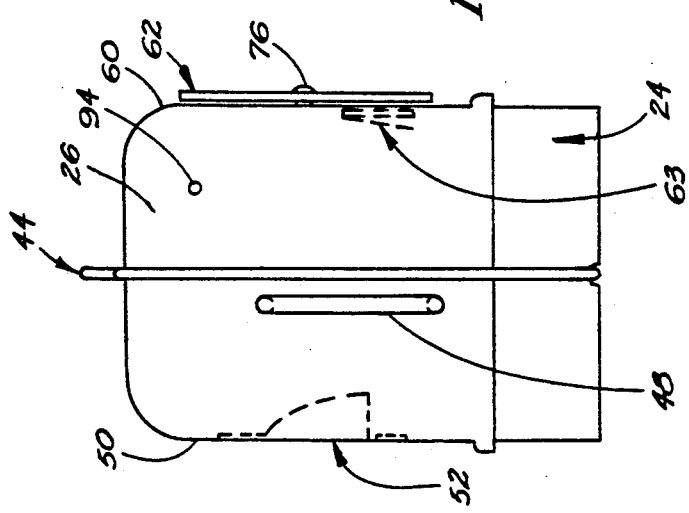
FIG. 2 is a right side elevational view of FIG. 1.
Figure 1:
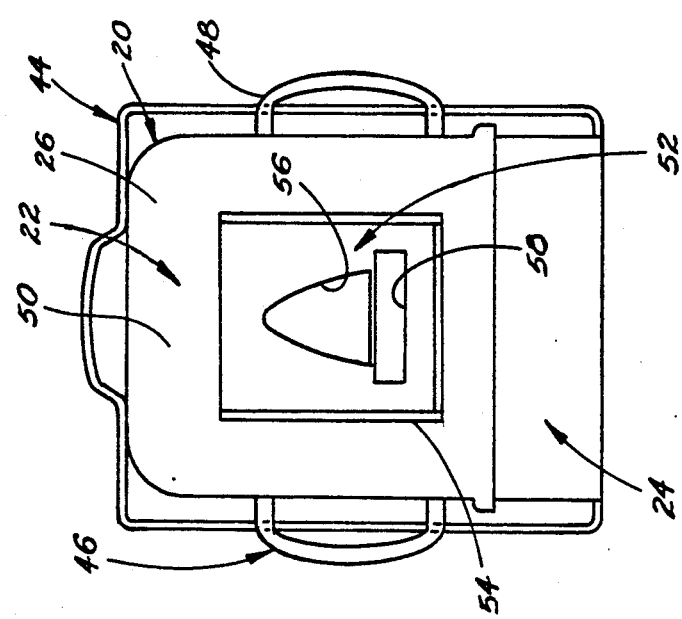
FIG. 1 is a front elevational view of an exemplary embodiment of apparatus embodying the invention.

FIGS. 1-3 show an exemplary form of therapeutic apparatus 20 according to the present invention. Apparatus 20 comprises a generally rectangular-shaped enclosure 22 that is cooperatively defined by a generally rectangular bottom piece in the form of an open-top pan 24 and a generally rectangular top piece in the form of an open-bottom cover 26.

Figure 14:
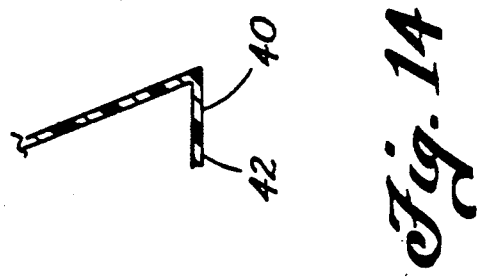
FIG. 14 is an enlarged fragmentary cross sectional view in the direction of arrows 14—14 in FIG. 12.
Figure 13:
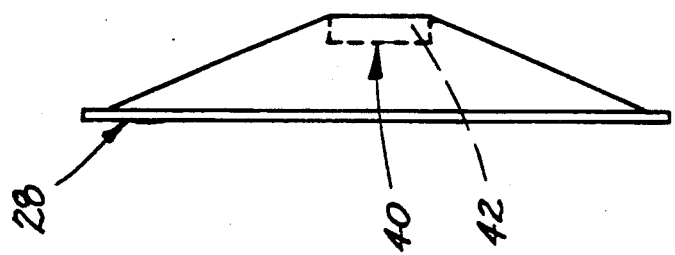
FIG. 13 is a right side elevational view of FIG. 12.
Figure 12:
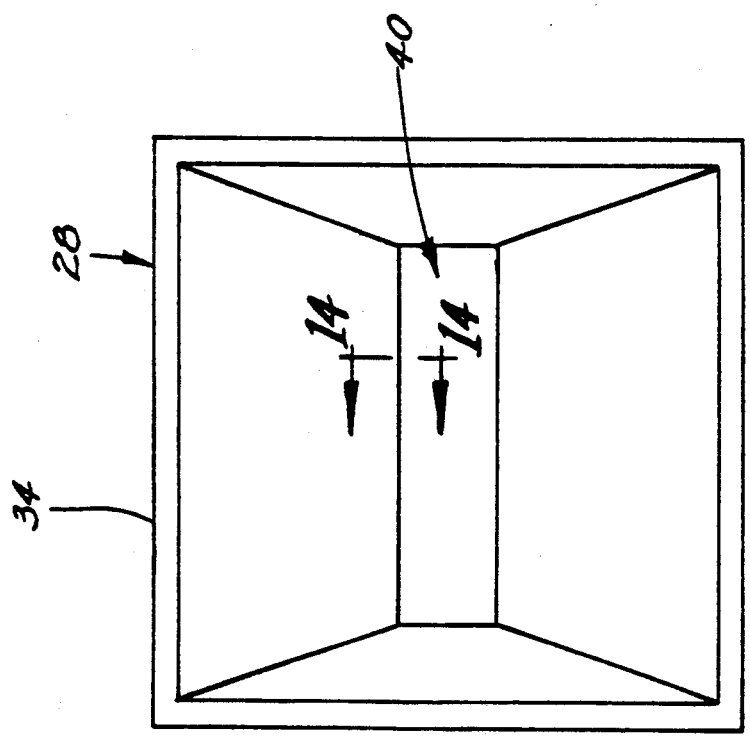
FIG. 12 is a bottom plan view of still another of the parts.

On the interior of enclosure 22, there is a dividing piece in the form of a perforate partition 28 which is shown by itself in FIGS. 12-14. Partition 28 divides the interior of enclosure 22 into a lower chamber 30 and an upper chamber 32, as shown in FIG. 17. Lower chamber 30 is cooperatively defined by partition 28 and pan 24 while upper chamber 32 is cooperatively defined by partition 28 and cover 26. Partition 28 may be held tight on pan 24 through means, such as springs, snaps, or hinges, which are not shown in the drawings.

FIG. 17 shows detail of the joint where the three parts 24, 26, and 28 fit together. Partition 28 has a perimeter margin 34 that rests on an internal ledge 36 extending around the inside of the upper edge of pan 24 whereby the partition is separably supported on the upper edge of the pan. The lower edge of cover 26 has a perimeter channel 38 that fits onto the pan's upper edge, entrapping margin 34 in the process.

As shown in FIGS. 12-14, partition 28 is somewhat roof-shaped, having four sloping sides extending inwardly and upwardly from margin 34 to a central rectangular opening 40. The edge of opening 40 comprises a downturned flange 42.

As shown by FIGS. 1-3, the three parts 24, 26, and 28 are held in assembly by an exterior metal handle member 44 that connects to the bottom of pan 24, extends upwardly along both opposite sides of enclosure 22, and across the top of cover 26, engaging the latter in the process by rolling into a groove. Alternately, snaps could be used for the attachment. Cover 26 is also provided with two handles 46 and 48 on its opposite sides. None of the handles appear in FIG. 3 for the sake of illustrative convenience in placing this FIG. next to FIG. 2 on the common drawing sheet.

The front wall 50 of cover 26 comprises a nasal piece, or panel, 52 that has accommodations for the nose and mouth of a user. FIG. 1 shows panel 52 separably mounted on front wall 50 by sliding fit into a groove 54 designed to hold it. The accommodation in panel 52 for the nose of a user comprise an aperture 56 through which the nose can be inserted into upper chamber 32, as shown in phantom in FIG. 5. The accommodation for the lips may also comprise an aperture 58, as shown in FIG. 1, but optionally may be closed so that only aperture 56 is present. The bridge of the nose may be protected from steam by a plastic wall 59 (FIG. 5 only) which gives a place for the nose to be placed. Different sizes and shapes for panel 52 allow the user to choose the way he or she wants to use the apparatus, as well as adapting to the nose size. In some models, there can be a soft cushion, either air-filled soft plastic or sponge-like materials, around the apertures which the facial parts touch. Instead of the use of a groove 54 for separably mounting panel 52 on front wall 50, connecting hooks 57, such as shown in FIGS. 4, 6, and 7 may be used for the separable mounting by hooking into slots in cover 26.

The rear wall 60 of cover 26 contains a means for selectively communicating upper chamber 32 to surrounding exterior space. This means comprises a multi-apertured rotary member 62 on the exterior and a slide assembly 63 on the interior.

Rotary member 62 is shown by itself in FIGS. 8 and 9 and comprises a plastic disk having five differently sized apertures 64, 66, 68, 70, and 72 distributed circumferentially around it. At its center, the disk comprises an apertured hub 74 via which it mounts for rotary motion about a horizontal shaft 76 (FIGS. 2 and 3). The disk is positionable to select any particular one of its five apertures via which chamber 32 communicates to the surrounding exterior space. In its outer edge, the disk has a series of five notches 77 associated with the five apertures to selectively coincide with a small elevated part (not shown) on the outside of rear wall portion 60 for keeping the rotary disk in a selected circumferential position; in other words, a detent feature.

Slide assembly 63 comprises a rectangular-shaped slide 78 that is mounted on the inside of wall 60 for horizontal sliding motion on upper and lower grooves (not shown). Slide 78 contains a two spaced apart openings 80 and 82. Opening 80 is a square in the slide. Opening 82 is also a square opening in the slide, but is bounded by a tapered flange 84 on the inside and covered on the inside by a flapper door 86. The flapper door depends from a horizontal hinge 88 and by force of gravity rests against the edge of tapered flange 84 to normally close opening 82; it functions as a one-way valve to allow flow into upper chamber 32.

The purpose of slide assembly 63 is to select either one-way (uni-directional) or two-way (bi-directional) communication of upper chamber 32 with the surrounding exterior space via a particular aperture of member 62 that has been elected to control the amount of air that is allowed to pass into the chamber.

The bottom of pan 24 is flat so that in use, it may be placed flat on a horizontal surface, such as a table top. Hot water is placed in pan 24, and partition 28 and cover 26 are placed over the pan and secured by handle member 44. Steam generated by the hot water in pan 24 rises upwardly, passing from lower chamber 30 through opening 40 and into upper chamber 32. The user inserts the nose through aperture 52 and inhales steam from the upper chamber. If slide assembly 63 has been operated to the position that selects opening 80, then there is bi-directional communication through the particular aperture of rotary member 62 that has been selected. If slide has instead been operated to the position that selects opening 82 and flapper door 86, there is only uni-directional communication whereby air can enter upper chamber 32 through the selected aperture opening of member 62, but not exit so that when the user inhales, air will be drawn into the enclosure through the flapper door opening, and when he exhales the door will close.

The apparatus is fabricated with the use of conventional materials such as plastic and metal. The roof-shape of partition 28 and the inclusion of flange 42 around opening 40 are advantageous in resisting the entrance of hot liquid into the upper chamber, such as may occur due to accidental tipping or splashing.

Certain optional features may be provided. One such feature is a heater, an electric heater for example, for keeping the water in the pan hot; it is represented by the numeral 90 in FIG. 16. The pan may be insulated by plastic or air layer insulation to retain heat. An alternate means of keeping hot water in the pan is by using a tubing system to bring hot water from a source and suction it out, and such a feature is represented by the numeral 92 in FIG. 16. Where a user needs more oxygen concentration inside the enclosure, it may have means, such as an opening in the wall that allows for connection of an oxygen tube, as represented by the numeral 94 in FIG. 2. As an alternate to the flapper door type of one-way valve, a caged ball type valve may be used, having a light-weight ball inside a cage that moves to open and close the valve.

It should be appreciated that the drawings are intended to be illustrative of principles of the invention.

What is claimed is:

1. Therapeutic apparatus for the nasal inhalation of steam by a user comprising: an enclosure cooperatively defined by an open-top pan and a removable cover, said enclosure defining inner volume means for holding hot water and steam, said enclosure further comprising a first wall portion and a second wall portion, said first wall portion having a nose-accommodating aperture means for allowing the user's nose to substantially sealingly project into said inner volume means and for allowing the inhalation of steam from the inner volume means by the user, and said second wall portion further comprising selection means for selectively communicating said inner volume means to the ambient.

2. Therapeutic apparatus as set forth in claim 1 wherein said first wall portion further comprises a detachable panel, said detachable panel including said nose-accommodating aperture means.

3. Therapeutic apparatus as set forth in claim 2 wherein said panel further comprises means for accommodating the lips of the user.

4. Therapeutic apparatus as set forth in claim 2 wherein said removable cover includes said first wall portion and said panel.

5. Therapeutic apparatus as set forth in claim 1 wherein said selection means further comprises selectable aperture means mounted on said second wall portion for selecting a particular sized aperture for communicating said inner volume means with the ambient, said selectable aperture means further including flow direction selection means for selecting between unidirectional or bidirectional flow between the inner volume means and the ambient.

6. Therapeutic apparatus as set forth in claim 5 wherein said selectable aperture means further comprises a rotary disk having a plurality of apertures distributed about the circumference, and wherein said flow direction selection means comprises a slide assembly mounted on said enclosure.

7. Therapeutic apparatus as set forth in claim 6 wherein said cover includes an inner and an outer surface, and wherein said disk is disposed on said outer surface and said slide assembly is mounted on said inner surface.

8. Therapeutic apparatus as set forth in claim 1 wherein said enclosure further comprises a perforate partition disposed within said inner volume means between said open-top pan and said removable cover.

9. Therapeutic apparatus as set forth in claim 8 wherein said perforate partition further comprises a pair of substantially equally sized planar members each joined along an edge to the other in angular fashion so as to form an apex, and a central opening formed along said apex.

10. Therapeutic apparatus as set forth in claim 1 further including water delivery and extraction means for adjusting the level of the hot water within said inner volume means.

11. Therapeutic apparatus as set forth in claim 1 further including a heater disposed within said open-top pan.

12. Therapeutic apparatus as set forth in claim 1 further comprising oxygen delivery means for providing oxygen to said inner volume means, said oxygen delivery means including an opening communicating with said inner volume means.

13. Therapeutic apparatus for the nasal inhalation of steam by a user comprising: an enclosure cooperatively defined by an open-top pan and a removable cover, said further comprising a first wall portion and a second wall portion, said first wall portion having means for allowing the user's nose to substantially sealingly inhale steam from the inner volume means and said second wall portion further comprising selection means for selectively communicating said inner volume means to the ambient, wherein said selection means further comprises selectable aperture means mounted on said second wall portion for selecting a particular sized aperture for communicating said inner volume means with the ambient, said selectable aperture means further including flow direction selection means for selecting between unidirectional or bidirectional flow between the inner volume means and the ambient.

14. Therapeutic apparatus as set forth in claim 13 wherein said selectable aperture means further comprises a rotary disk having a plurality of apertures distributed about the circumference, and wherein said flow direction selection means comprises a slide assembly mounted on said enclosure.

15. Therapeutic apparatus as set forth in claim 14 wherein said includes an inner and an outer surface, and wherein said disk is disposed on said outer surface and said slide assembly is mounted on said inner surface.

16. Therapeutic apparatus as set forth in claim 13 wherein said enclosure further comprises a perforate partition disposed within said inner volume means between said open-top pan and said removable cover.

17. Therapeutic apparatus as set forth in claim 16 wherein said perforate partition further comprises a pair of substantially equally sized planar members each joined along an edge to the other in angular fashion so as to form an apex, and a central opening formed along said apex.

18. Therapeutic apparatus as set forth in claim 13 further including water delivery and extraction means for adjusting the level of the hot water within said inner volume means.

19. Therapeutic apparatus as set forth in claim 13 further including a heater disposed within said open-top pan.

20. Therapeutic apparatus as set forth in claim 13 further comprising oxygen delivery means for providing oxygen to said inner volume means, said oxygen delivery means including an opening communicating with said inner volume.

* * * * *